(12) United States Patent
Shenberg

(10) Patent No.: US 9,220,800 B2
(45) Date of Patent: Dec. 29, 2015

(54) BOTTLED OZONATED WATER SYSTEM

(75) Inventor: James E. Shenberg, Santa Monica, CA (US)

(73) Assignee: THEROZONE USA, INC., Santa Monica, CA (US)

( * ) Notice: Subject to any disclaimer, the term of this patent is extended or adjusted under 35 U.S.C. 154(b) by 36 days.

(21) Appl. No.: 13/016,737

(22) Filed: Jan. 28, 2011

(65) Prior Publication Data

US 2012/0039751 A1 Feb. 16, 2012

Related U.S. Application Data

(60) Provisional application No. 61/299,897, filed on Jan. 29, 2010.

(51) Int. Cl.
| | | |
|---|---|---|
| *B01D 35/00* | (2006.01) | |
| *B01D 21/24* | (2006.01) | |
| *B01D 27/00* | (2006.01) | |
| *A61L 2/18* | (2006.01) | |
| *C02F 1/78* | (2006.01) | |
| *A61L 2/20* | (2006.01) | |

(52) U.S. Cl.
CPC . *A61L 2/183* (2013.01); *C02F 1/78* (2013.01); *A61L 2/18* (2013.01); *A61L 2/202* (2013.01); *C02F 2201/78* (2013.01); *C02F 2201/782* (2013.01); *C02F 2201/784* (2013.01)

(58) Field of Classification Search
None
See application file for complete search history.

(56) References Cited

U.S. PATENT DOCUMENTS

| | | | | |
|---|---|---|---|---|
| 3,756,410 | A | * 9/1973 | Moody et al. | 210/139 |
| 5,366,619 | A | 11/1994 | Matsui et al. | |
| 6,585,898 | B1 | * 7/2003 | Ekberg et al. | 210/760 |
| 2003/0207056 | A1 | * 11/2003 | Wood et al. | 428/35.7 |
| 2005/0017380 | A1 | 1/2005 | Namespetra et al. | |

FOREIGN PATENT DOCUMENTS

| | | |
|---|---|---|
| CN | 201192474 | 2/2009 |
| WO | WO02/051739 | 7/2002 |
| WO | WO2006/096991 | 9/2006 |

OTHER PUBLICATIONS

Annex, partial Search Report of International Application No. PCT/US2011/000165 mailed May 6, 2011.

* cited by examiner

*Primary Examiner* — Nam Nguyen
*Assistant Examiner* — Richard Gurtowski
(74) *Attorney, Agent, or Firm* — Koppel, Patrick, Heybl & Philpott; Michael J. Ram

(57) ABSTRACT

A dissolved ozone delivery system comprises a generator for producing gaseous ozone, a bottle for holding a liquid suitable for receiving the gaseous ozone, flow conduits for delivering the gaseous ozone to the bottle and dissolving the ozone into the liquid to form an ozonated liquid, and a multicomponent bottle closure sealing device. The multicomponent bottle closure sealing has several discrete gas flow passageways for channeling the ozone gas into the bottle, venting undissolved gas and delivering the ozonated liquid to an exterior surface for decontamination thereof or medical instruments for sterilization or use in medical or dental procedures.

7 Claims, 12 Drawing Sheets

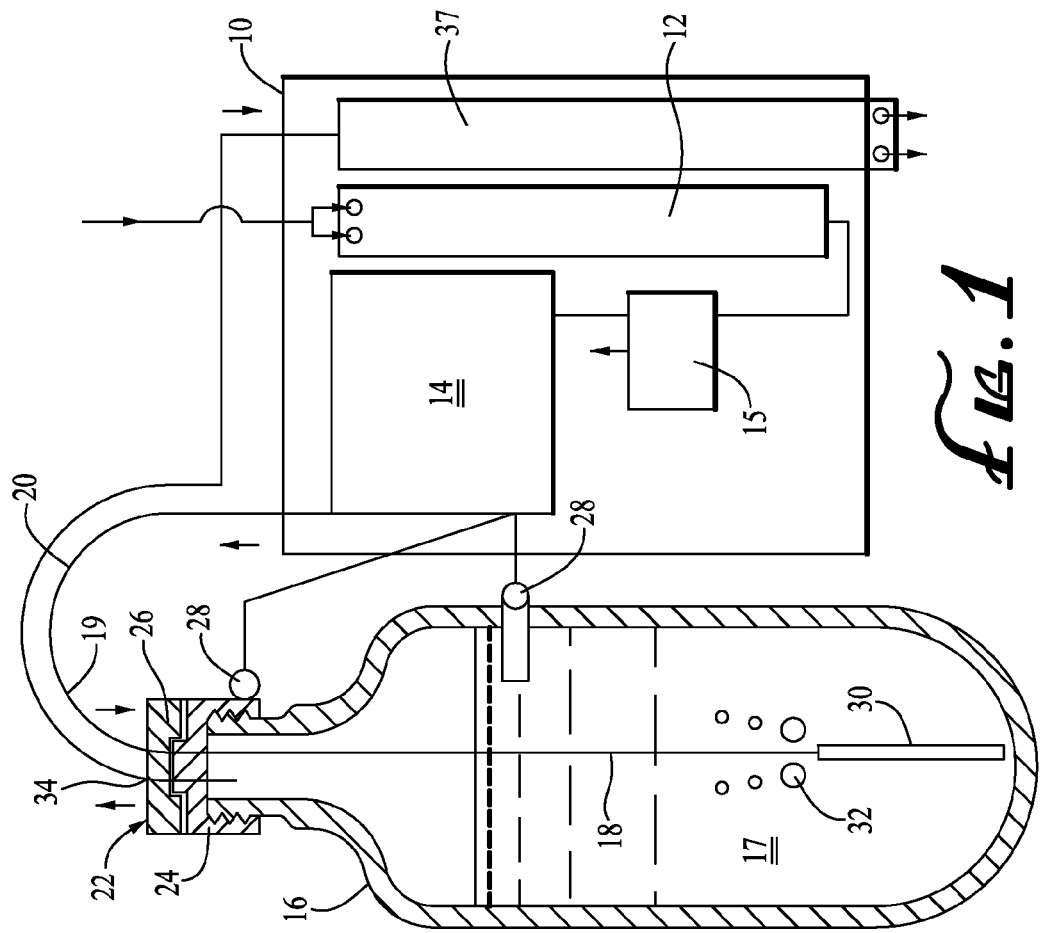
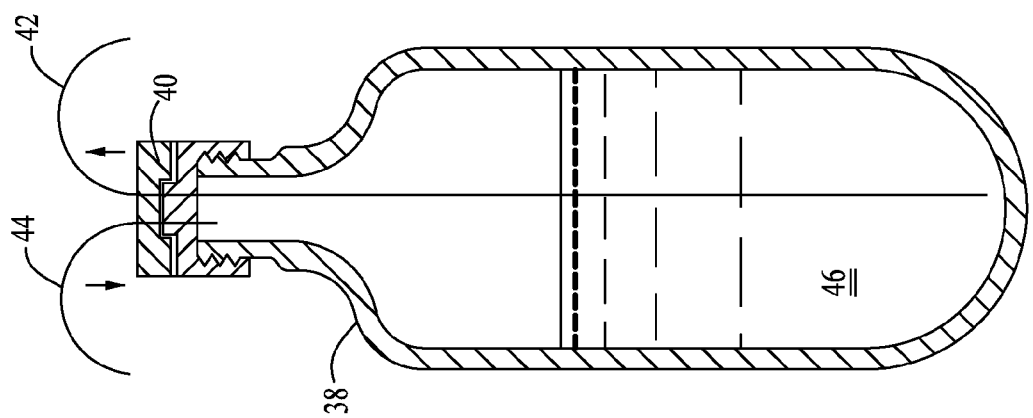

BOTTLED OZONATED WATER SYSTEM

Benefit of U.S. Provisional Application No. 61/299,897, filed Jan. 29, 2010 is claimed.

The present invention relates to a system for introducing ozone into bottles of water and dissolving the ozone in the water. The ozonated water can be used for various applications such as dental and medical procedures, particularly dental irrigation, as well as cleaning and decontaminating surfaces, particularly exterior and interior surfaces of dental and medical equipment.

BACKGROUND

It is well known that ozone is useful as a disinfectant for killing bacteria, viruses and mold spores and rendering harmless contaminates that are on instrument, device surfaces and food products as well as contaminants which may be present in the air. There have been disclosures of the use of ozone in the treatment of wounds, and there are numerous publications, primarily in Europe, directed to the use of ozone in dental procedures to aid in healing of dental conditions.

One problem in working with ozonated water is that ozone dissolved in water rapidly decays to oxygen. Depending on the concentration of the ozone and the temperature of the water, the half-life (useful life) of the ozonated water can be from 3 days to as little as 30 minute; at elevated temperatures decomposition is more rapid. Therefore, ozone can not be readily bottled for extended storage and later use. Also, ozone is considered to be a toxic substance and inhalation or unintended skin contact can be harmful. It is therefore desirable to manufacture ozone, dissolve it in water and use the ozone/water composition, that is, bring it into contact with the dental surfaces to be treated, as quickly as possible and then decompose the excess or used ozone so that it does not create a health hazard. Further, it is desirable to reduce the amount of ozone that must be generated by maximizing the efficiency of dissolving the ozone that is generated into water for use in the decontamination process.

Bacteria that causes tooth decay is found deep within the tooth structure. Ozone is effective in the reduction of bacteria from tooth surfaces or around the gum line and is better and more effective than chlorine based disinfectants. Ozone also has value in tooth whitening as well as reducing tooth sensitivity, gum line pockets, gum line irritation, halitosis and has been shown to assist in the reversal of the decay process in shallow, initial cavities as well as infections deep within the root as part of endodontic procedures.

Since 1998 Professor Edward Lynch, Queen's Dental Hospital and Belfast University, Ireland, has been demonstrating the utility of ozone in dental procedures. It destroys organic effluents that are produced by these bacteria. By effectively sterilizing the lesion, minerals from the patient's own saliva then remineralizes the areas of mineral loss, also hardening the tooth. Once the tooth is hardened, it is more resistant to future bacterial attack and mineral loss.

Studies from Europe (Abu-Salem et al, 2003; Baysan and Lynch 2001; Holmes, 2003; Holmes and Lynch, 2003) have demonstrated that the use of ozone in dental care is effective as a non-destructive method to manage decay and its destructive effects. The effects of ozone reduce tooth destruction in routine procedures (Clifford, 2004; Holmes, 2004; Holmes and Lynch, 2004) and ozone reduces the time and the cost of dental care (Domingo and Holmes, 2004; Johnson et al, 2003). In Endodontics, ozone is effective against *Enterococcus faecalis* (Chang et al, 2003).

It is also known that water supply passageways, even for the supply of purified water, will develop a bacterial or fungal growth on their inner surfaces, referred to as a biofilm. For example, dental units used to supply rinse water to the mouth of a patient can often be contaminated unless particular efforts are made to disinfect and clean the water supply lines. Test show that, if not properly maintained, these water supply systems may have bacterial counts in excess of one million colony forming units of bacteria per millimeter of water (>1× $10^6$ CFU/ml). While bacterial counts in dental units are generally less then $1 \times 10^6$, they are usually far in excess of the American Dental Association recommended bacterial levels of below 200 CFU/ml in dental water supply systems. The source of the bacterial contamination may be the supply water or back splatter from the irrigation fluids sprayed into the patient's mouth. In spite of over 35 years of scientific and clinical studies worldwide, it is estimated over 30 percent of the dental units still use city water as a source. As a result, there are over 300,000 contaminated patient treatment sites in the US alone. Of further concern, even though certain dental units use bottles of sterile water is that they are often refilled with city water, defeating the intended purpose of using prebottled pure water. Still further some units allow the mounting of two bottles one of which is usually filled with city water. A further inadequate alternative is to use city water and add a decontaminating agent, such as silver iodide or other microbiocides, to each bottle of water. This may decontaminate the water but then the patients will also be exposed to the chemicals.

U.S. Pat. No. 6,857,436 to Labib et al discloses a method of cleaning small passageways in a fluid distribution system such as a dental water supply unit, endoscopes, biopsy devices, heat exchangers, micro-filtration, ultra-filtration, dialysis and reverse osmosis equipment. US Published Application 2006/0191849 to Garrison et al is directed to a method of cleaning a dental unit water system using a silver colloid, hydrogen peroxide composition.

U.S. Pat. No. 6,585,898 to Ekberg et al. is an example of a device for the production of water which includes dissolved ozone. The ozone generated by the use of a plasma resonance electrode is added to pure water by a combination of diffusion and injector technology. The system appears to recirculate the water solution until a desired ozone concentration is reached (1.5-2 ppm). One disclosed application is the cleaning or sterilization of a medical instrument. To do so a spray bottle is filled with the ozone-water mixture. Alternatively, ozone gas is feed into a contaminated, water filled container to decontaminate the container.

The need for a simple and effective method and system to prepare bottled ozonated water for various applications including, but not limited to, providing ozonated water for dental and medical procedures and decontamination of medical and dental devices as well as dental irrigation systems has clearly been shown. Previous devices or systems have not be found to be acceptable because they are too difficult to use, too large for use in dental or medical procedures or do not provide and effective treatment without leaving residual chemicals that may be detrimental to the patient.

SUMMARY

A compact ozone generator that generates large quantities of ozone in a relatively short time feeds the ozone into bottles of water attached to the device so that the ozone dissolves in the water. Also disclosed is a bottle cap specifically designed to receive the ozone gas and bubble that ozone gas through water enclosed within the bottle. The bottle cap or a part of the bottle cap is also designed for decoupling from the compact ozone generator and then receiving a dispensing instrument for delivering the ozonated water for use in instrument decontamination or dental procedures. Once a desired ozone concentration in the water is reached, the bottle is disconnected from the ozone generator and attached to a delivery system for application of ozonated water to the intended surface. Additional bottles of water can be attached to the ozone generator so that a continuous supply of bottles with ozonated water can be available.

DESCRIPTION OF THE DRAWINGS

FIG. 1 is a cutaway schematic drawing showing the major components of an ozone generation and delivery system with a bottle attached incorporating features of the invention.

FIG. 2 is a cutaway schematic representation of a bottle of ozonated water after detachment from the ozone generator, the bottle configured for delivery of the ozonated water.

DETAILED DESCRIPTION

Figure 3:
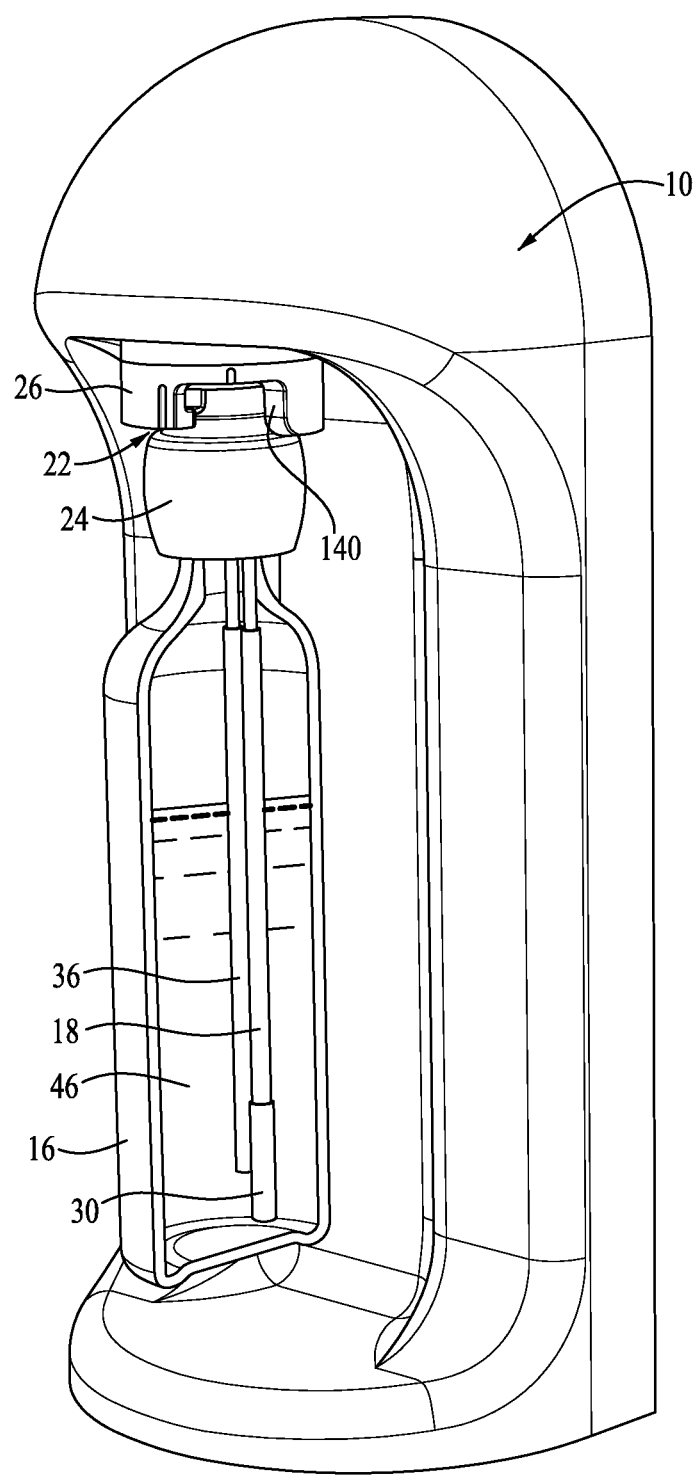
FIG. 3 is a partially cutaway perspective view of a bottle of ozonated water such as shown in FIG. 2 and FIG. 13 attached to a holding stand of an ozone generator and charging unit.

A device for producing bottles of water with ozone dissolved therein is described. Once the sufficient ozone has been dissolved in the water the bottles are disconnected from the ozone generating system, also referred to as charging station, and then connected to other devices for use in cleaning and disinfecting articles or for dental procedures. In one application the ozonated water is used to clean and disinfect small flow channels in various pieces of equipment, particularly medical devices and more particularly dental units. Once treated with ozone the dental units can also be used to provide a sterile oral rinse solution during a dental procedure. In another application the bottle of ozonated water is attached to a delivery device for directly applying the ozonated water to teeth of tissue in the mouth. However, as explained herein, the potential uses of the bottles of ozonated water produced using the system are not limited to dental units or dental applications.

An ozone generating and bottle filling/charging system 10, also referred as a bottle charging station, in its simplest configuration is shown schematically in FIG. 1. The arrows on FIG. 1 indicate the flow direction of the gaseous streams through the system. Atmospheric air, preferably filtered atmospheric air, is feed through a desiccant containing air drying device 12. The source gas can also be air or oxygen supplied from a pressurized tank or a centralized air or oxygen supply system or an oxygen generating or concentrating device. Alternatively, desiccated air may be provided by an appropriate compressor or pump. This source-gas is preferably supplied under pressure. However, if it is at ambient conditions, for example atmospheric air, it can be drawn into the system via the suction side of a pump 15 within the bottle charging station 10 or part of the ozone generator 14. Ozone can be generated by various techniques including, but not limited to a hot spark/corona discharge, ultraviolet light or a cold plasma. Various different commercially available ozone generators can be incorporated in the system. However a preferred ozone generator is a corona discharge unit. This ozone generator 14 and pump 15 attached thereto or included therein preferably continuously generates about 250 mg of ozone per hour from a ambient air stream fed to the ozone generator 14 at ambient conditions. In FIG. 1 the pump 15 is shown disposed between the desiccant air drying device 12 and the ozone generator 14. However, it can be positioned in other locations in the system, for example prior to the desiccant air drying device 12 to push the feed air through the system or after the ozone generator 14 to draw the air feed stream through the system. Still further, if the air fed into the system is pre-pressurized, such as bottled air or oxygen or a central compressed air or oxygen feed system, or a stream of gas with a greater concentration of oxygen is provided to the system under pressure it may be possible to eliminate the pump within the charging station 10 and rely on the pressure of the feed stream.

It is preferred that the feed stream to the ozone generator have an enhanced oxygen concentration. If a higher concentration oxygen steam is delivered to the ozone generator 14 then a greater amount of ozone can be generated over the same period of time or the same amount can be generated in a shorter time period. This can be accomplished by using bottled pressurized oxygen, or a centrally supplied, enhanced oxygen source such as available in a hospital or clinic setting.

Figure 13:
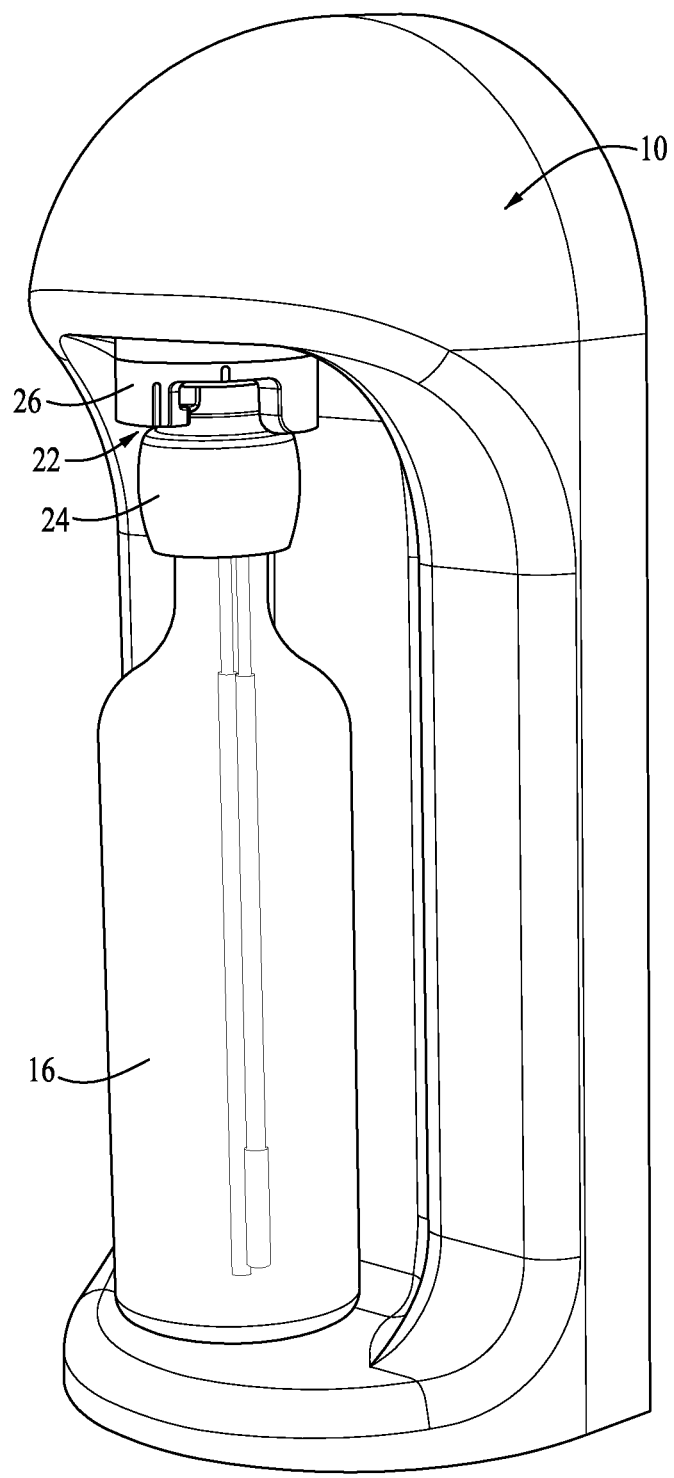
FIG. 13 is a perspective view of a bottle mounted to a charging stand to receive ozone.

A bottle 16 of liquid 17, preferably water (distilled, deionized, sterile, etc) and referred to herein after as water, containing from about 100 to about 1000 cc of water, is mounted to the charging station 10 as shown in FIGS. 3 and 13. The term "bottle" is used in its general sense and is not intended to limit the scope thereof to a glass container and, in fact, is intended to indicate any suitable container or vessel formed from any suitable material including, but not limited to, a glass, plastic or a metal container. Other suitable liquids or water solutions can be used. However, for simplicity of description, the liquid will be referred to as water. An ozone delivery tube 20 connects the output of the ozone generator to the feed tube connector 19 that passes through the top portion of a multi-component gas-tight stopper 22 attached to the bottle and into the feed tube 18 within bottle 16 to a point below the surface of the water 17. A preferred stopper 22, shown in a simple schematic form in FIGS. 1 and 2, preferably comprises at least two major components, namely a lower portion 24 for attachment to the bottle top exterior or for insertion into the top of the bottle 16 and an upper portion 26 to receive, in an air tight manner, the ozone delivery tube 20 from the ozone generator. Alternatively, the upper portion 26 of the stopper may have a delivery tube 20 pre-attached thereto. The upper portion 26 and lower portions 24, which can each comprise multiple components, are preferably configured as a quick connect/disconnect assembly or twist lock arrangement which creates an air tight seal on the top of the bottle 16. Preferred connect/disconnect stopper assemblies are described herein. The disclosed stopper arrangement allows the bottle 16 with ozonated water therein to be disconnected from the bottle charging station 10 or the upper portion of the stopper 26 for transferring the bottle with its contents to suitable delivery devices. The stopper can have valved openings (not shown) in the top to allow removal of the delivery tube 20 as well as an undissolved ozone return line or separation of the two parts of the stopper. The fittings 34 on the upper portion allow for connection of tubing for removing undissolved ozone 33 from the bottle. The undissolved ozone 33 can be fed to an ozone destruct system or recycled to the input side of the ozone generator, increasing the efficiency of ozone generation. In a preferred embodiment two tubes, discussed below, are permanently attached to the lower portion 24 of the stopper 22. A valving mechanism, such as pinch valve or turn valve (not shown) may be incorporated as part of the upper or lower portion 24, 26 of the stopper 22 to prevent loss of gaseous ozone from the bottle during transfer operations.

Figure 4:
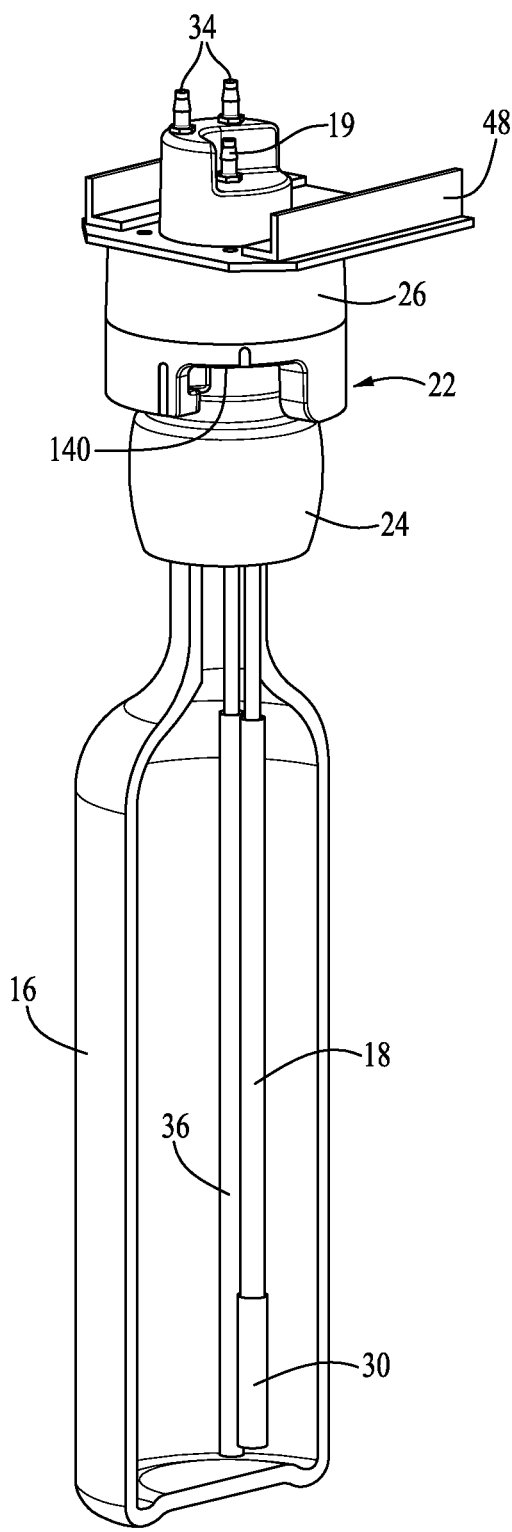
FIG. 4 is a partially cutaway perspective view of the bottle of ozonated water and stopper as shown in FIG. 3 configured for placing ozone in the bottle.
Figure 5:
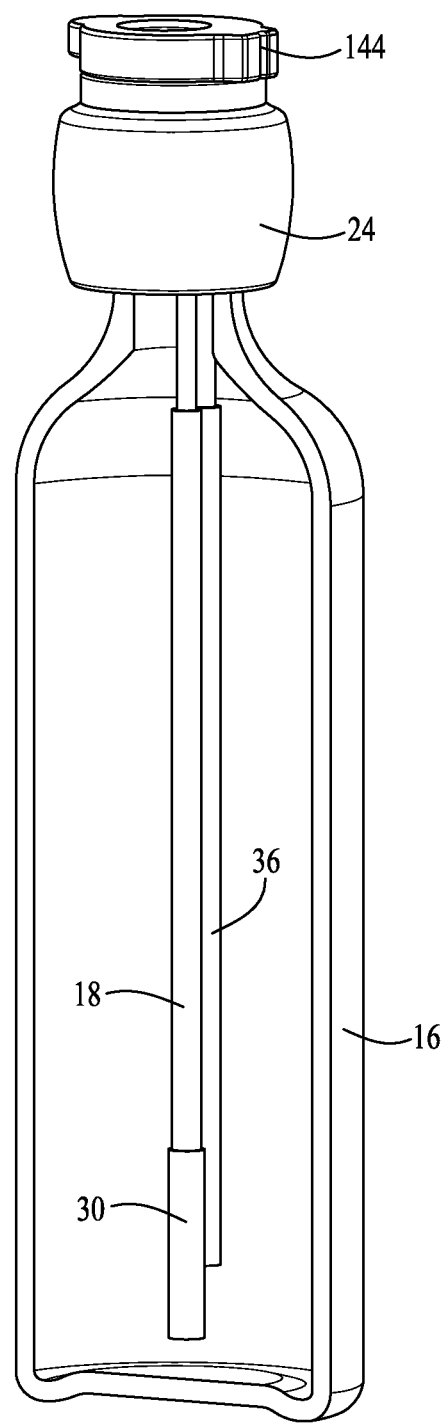
FIG. 5 is a partially cutaway view of the bottle of FIG. 3 with the lower stopper portion configured for placement of an ozonated water delivery device.
Figure 8:
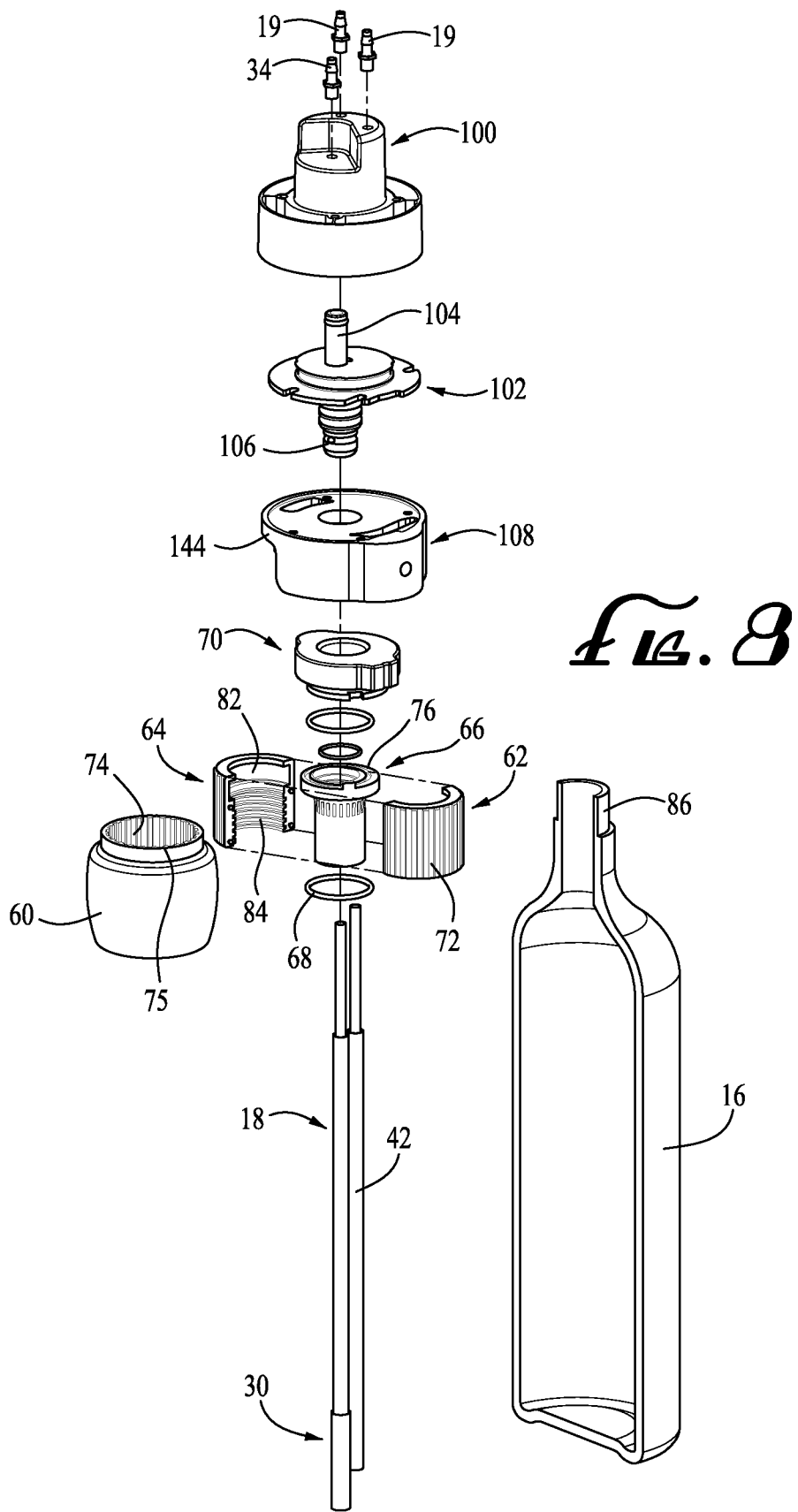
FIG. 8 is an expanded drawing showing the various components of the quick connect bottle stopper of FIGS. 6 and 7.
Figure 9:
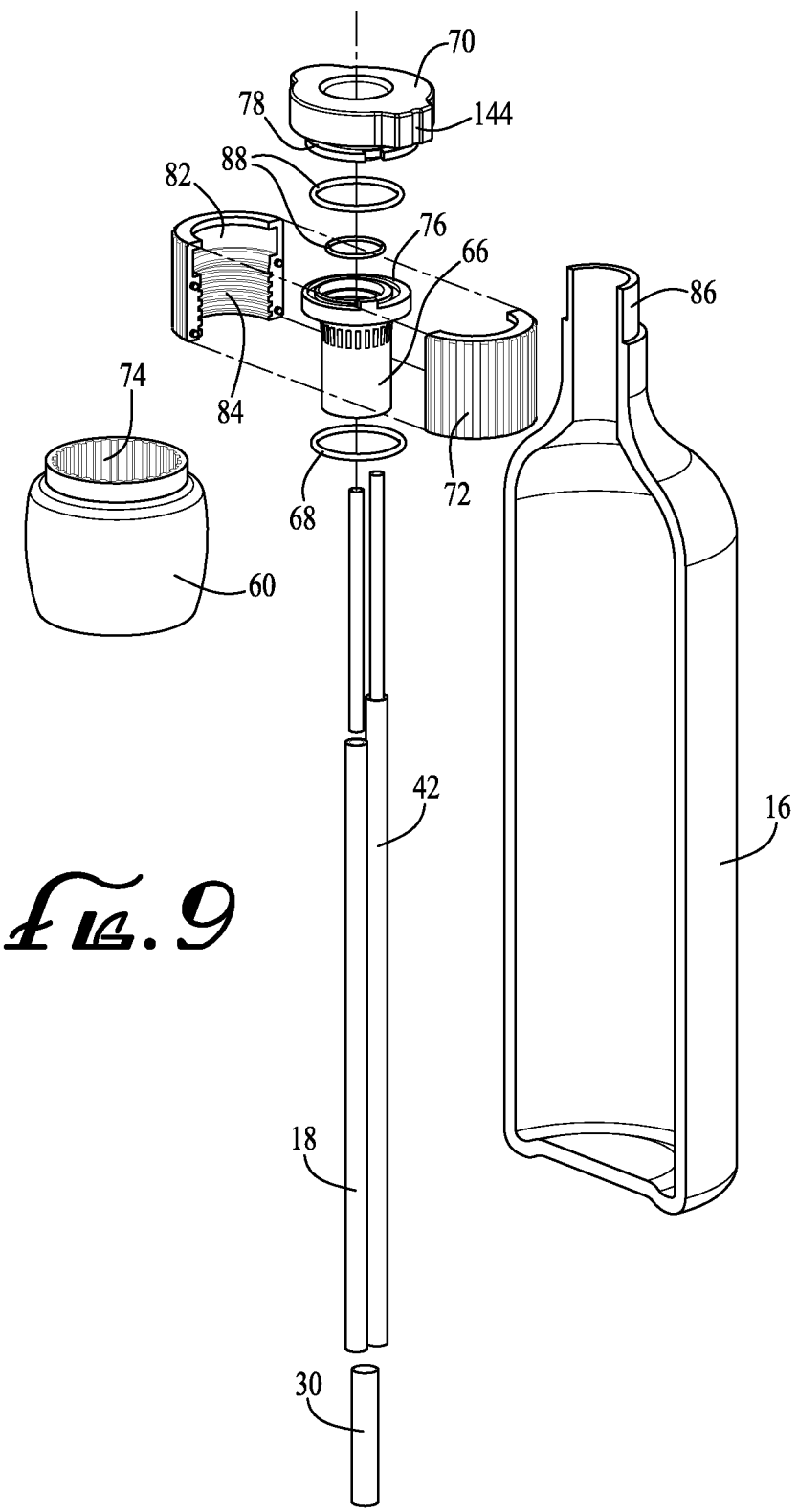
FIG. 9 is an enlarged expanded view of FIG. 6 showing the stopper lower portion.
Figure 10:
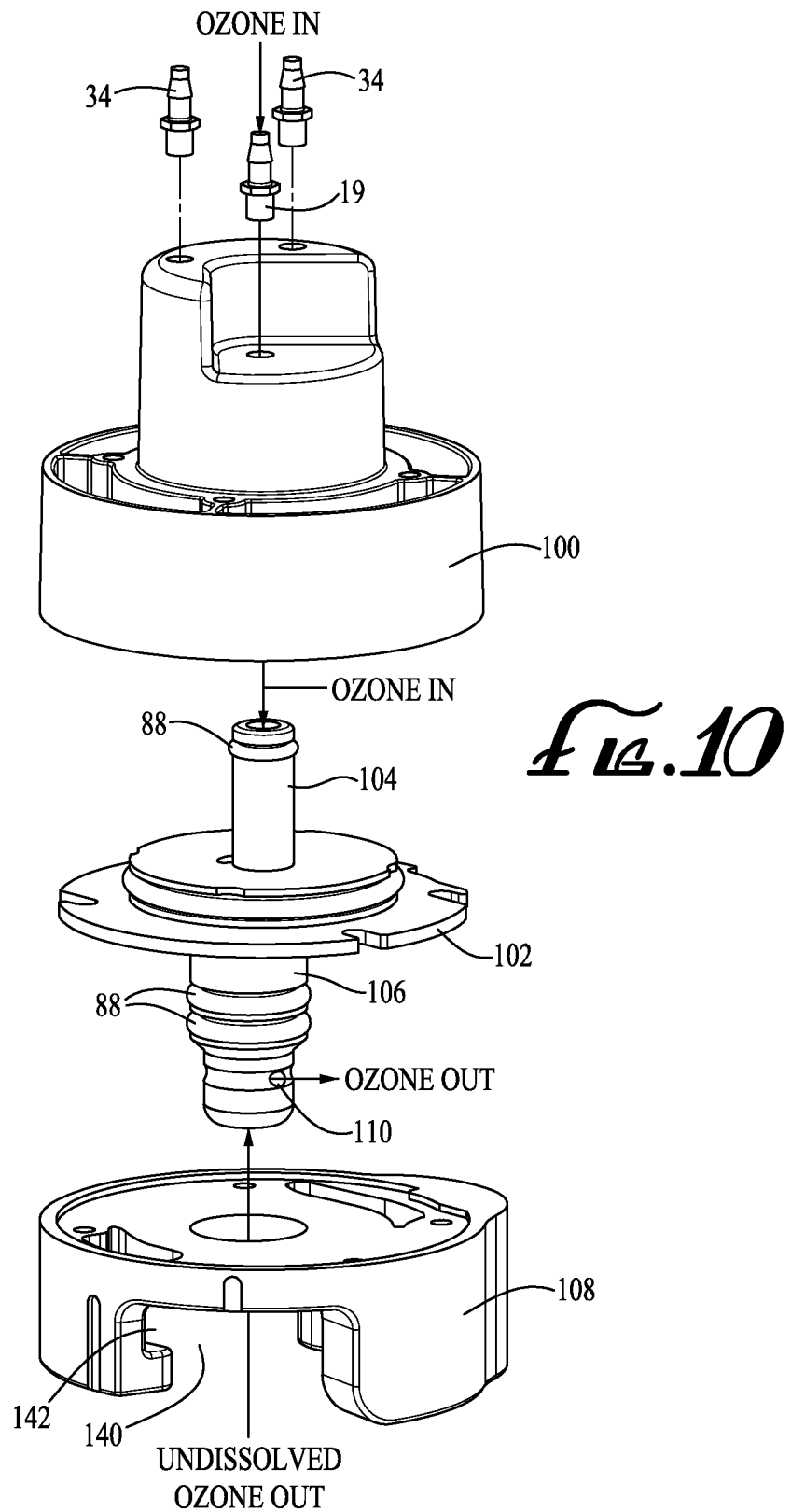
FIG. 10 is an enlarged expanded view of FIG. 8 showing the stopper upper portion.
Figure 11:
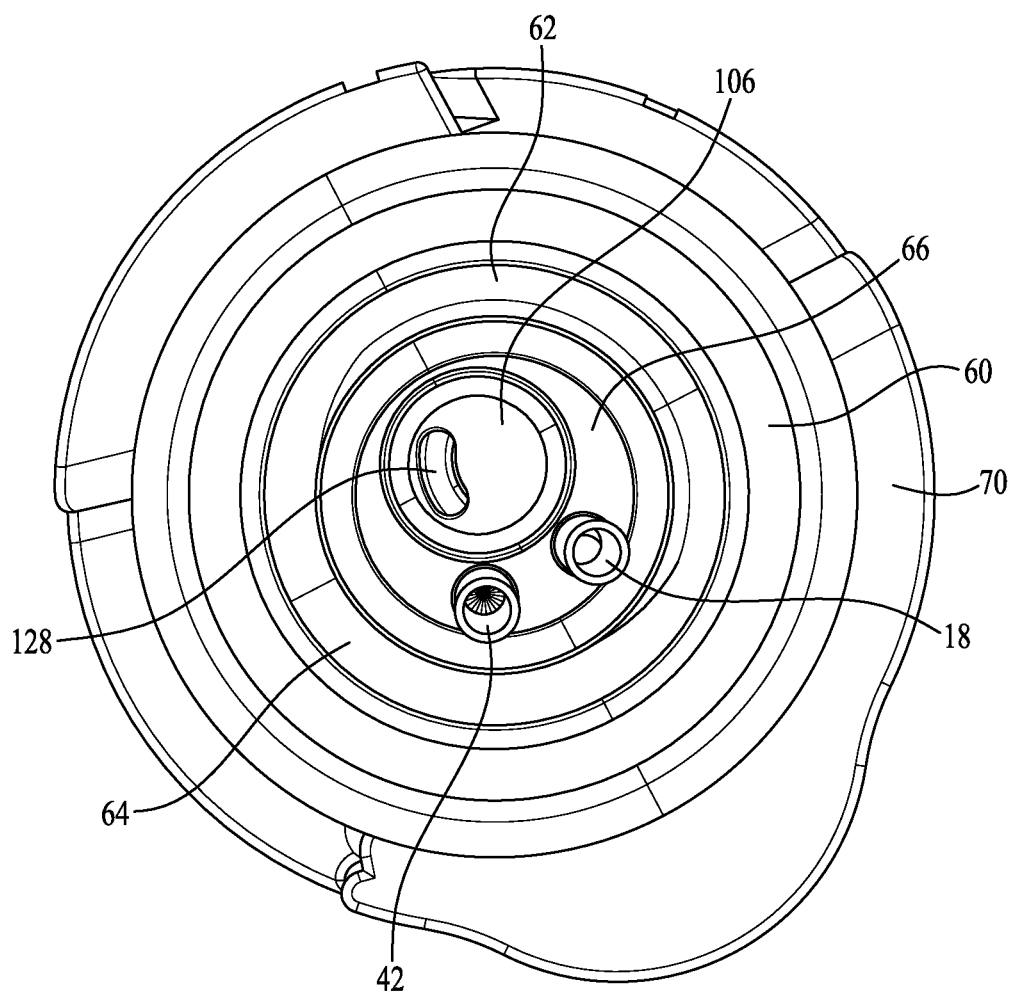
FIG. 11 is a bottom view of the lower stopper portion.

FIG. 4 is a partially cutaway view of a preferred stopper assembly mounted on the bottle 16 showing an ozone feed tube 18 with diffuser 30 and an ozonated water delivery tube 36 (which is the lower end of delivery line 42 shown in FIGS. 8, 9 and 11 extending from the stopper into the bottle. FIG. 5 shows the same assembly after removal of the top half of the stopper configured for attachment of a device for transfer of the ozonated water such as shown in FIG. 12.

As an added feature the bottle charging station 10 or a bottle holder 18 on the charging station 10 may include a sensor 28 which senses the presence of the bottle 16. FIG. 1 shows the sensor 28 positioned adjacent the normal location of the lower portion 24 of the stopper 22 to sense the presence of the stoppered bottle on the charging station 10 for filling. The sensor 28 may be a mechanical, electrical, optical, or other device capable of sensing the presence of an object (the bottle) in a certain position and then to turning on the ozone generator 12 in the charging station 10. As an added feature the sensor 28 or a second sensor 28 may also sense, by a level sensor or by measuring the bottle weight, whether the bottle 16 contains an adequate amount of water. The signal from the one or more sensors, upon sensing the presence of the bottle 16 in the ozone receiving position can then actuate the production of ozone by the ozone generator 14, and/or open a pinch tube or other type of valve located at the entrance to or exit from the ozone generator 14 or on the gas fed line to the system (values not shown) to commence generating ozone and filing the bottle. The presence of one or more sensors 28 can prevent the system from turning on if there is no water or inadequate water in the bottle. Still further the bottle holder 18 may include a weight sensing device which requires that the proper bottle, stopper and amount of water is present before ozone generation is commenced, thus preventing unsuitable containers being used to collect ozone. Switches/actuators are not more fully described because numerous suitable devices, incorporated herein by reference, are disclosed within the prior art.

Once the water filled bottle 16 is properly attached to the bottle charging station 10 the ozone generator 14 can be manually or automatically turned on and the ozone gas generated and fed under a controlled pressure through the tube 20 into the bottle 16. The ozone containing gas passes through the tube 20 and then through the diffuser 30 into the water 17 in the bottle. The diffuser 30 is preferably positioned near the bottom of the bottle to provide the greatest contact time between the ozone passing through the diffuser and the water. Some of the ozone containing gas stream 32 is thereby bubbled through the water 17 and becomes dissolved in the liquid to produce ozonated water. The ozone-containing gas 32 which is not dissolved in the water is vented through one or more return fittings 34. As indicated above, the undissolved ozone 33 can be delivered to an ozone destruction canister 37 which contains a catalyst, chemical or absorbent which will collect and/or decompose the ozone to regenerate oxygen which is then discharged from the canister. The prior art describes such ozone decomposing agents. Alternatively, the undissolved ozone 33 may be mixed with the feed stream fed into the desiccant filled air drying device 12 or into the ozone generator 14 for recycling.

Figure 6:
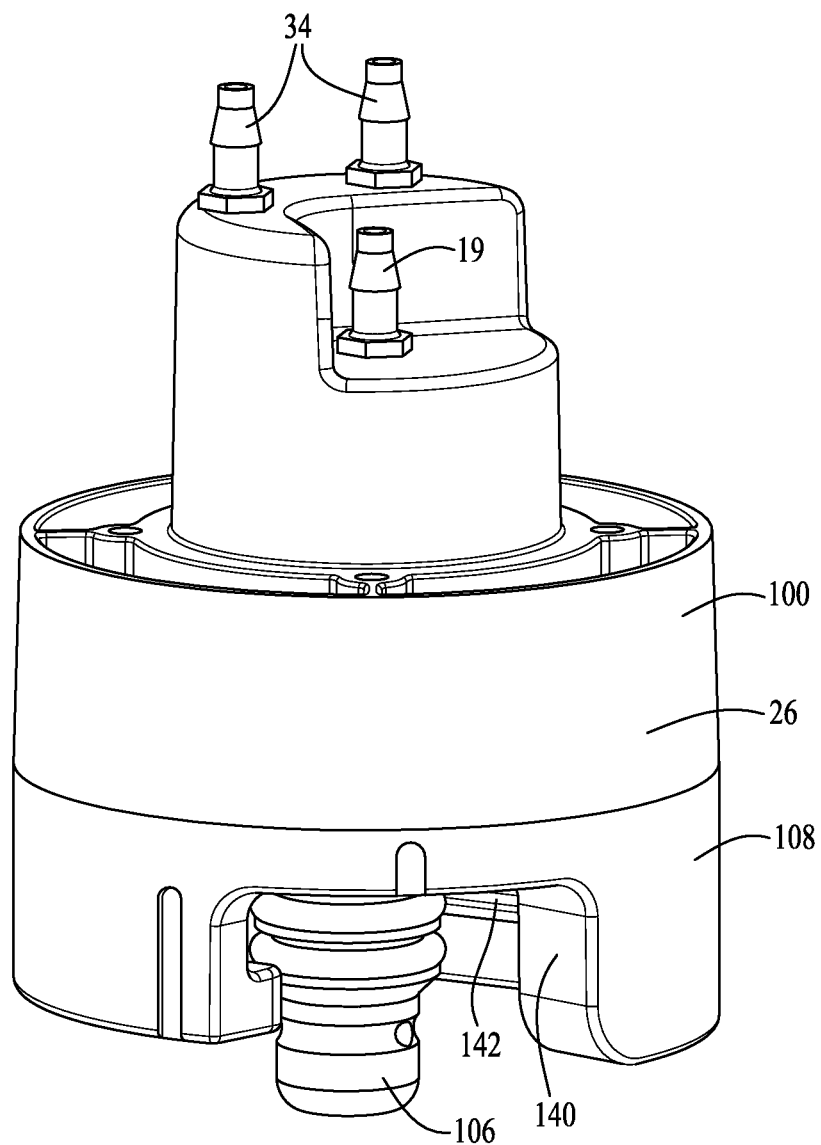
FIG. 6 is a perspective view of the bottle stopper upper portion.
Figure 12:
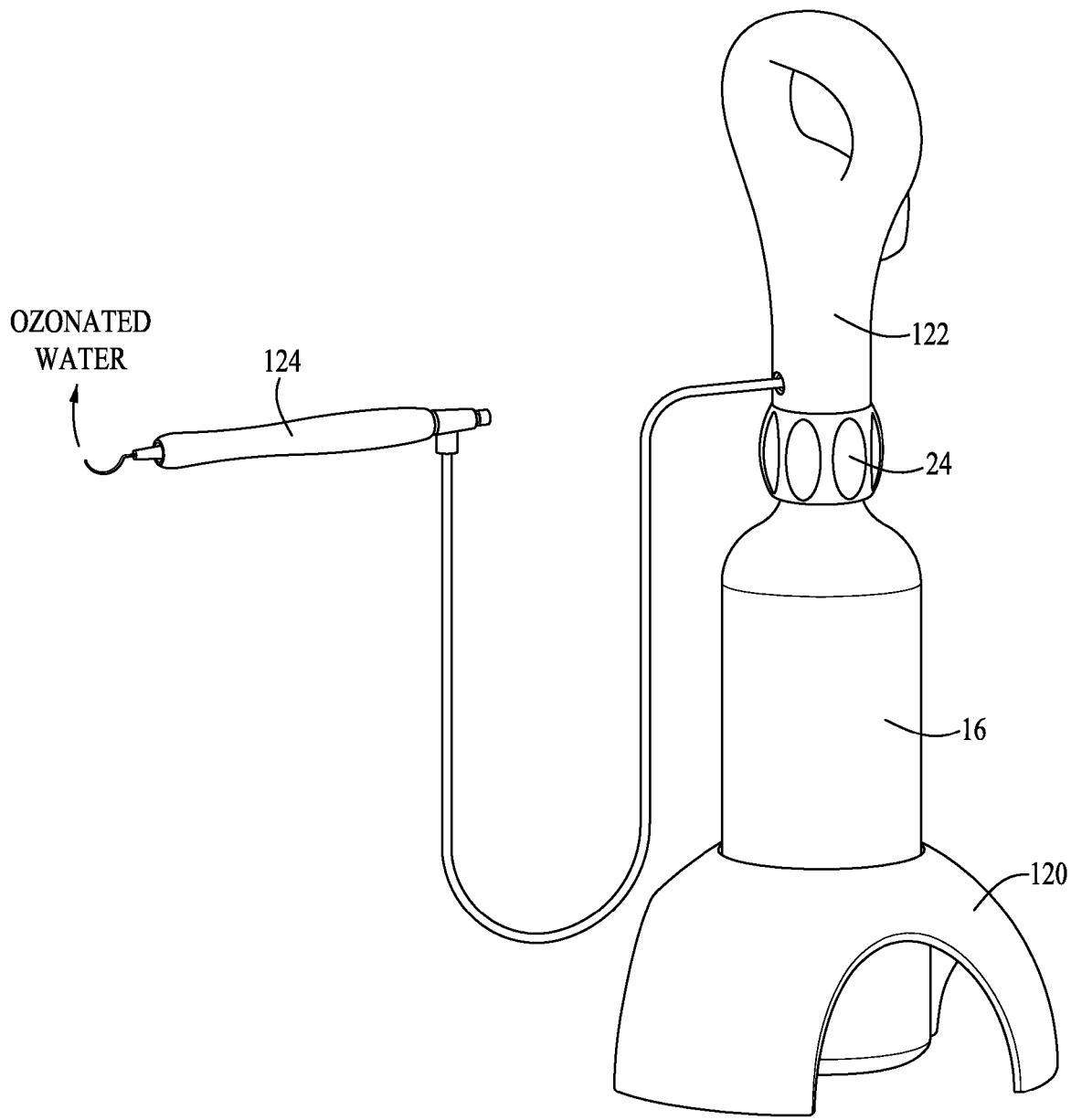
FIG. 12 is a perspective view of a bottle containing ozonated water such as shown in FIG. 5 placed in a holding stand with a dental irrigation device for delivery of ozonated water attached thereto.

After the dissolved ozone concentration in the water 17 in the bottle 16 has reached and acceptable level, preferably ≥2 ppm, the bottle 16 containing the ozonated water or fluid can be disconnected from upper portion 26 of the stopper (shown in FIG. 6 or otherwise separated from the bottle charging station 10 (see FIGS. 2 and 5) and joined to a delivery device, such as shown in FIG. 12 which includes a suitable mating connector. While the system does not show a detector to measure the level of dissolved ozone, a detector may be included within the bottle 16 or the ozonated water from the bottle can be placed in an ozone detection system or test strips can be used to verify ozone levels. Still further, the operation of the system has been standardized so that under fixed operating conditions (temperature, pressure feed gas characteristics, water quantity, etc. a charging time can be established that is known to produce the desired concentration of ozone in the water. These operating parameters and end results can be presented as a series of charts or graphs provided as part of the operating instructions so that each bottle of ozonated water does not have to be tested for ozone concentration. FIG. 2 schematically shows one embodiment of a charged bottle 38 with an upper delivery stopper 40 which has a delivery line 42 and a pressure line 44 attached thereto ready for attachment to a device for delivering the ozonated water 46. As an alternative, the bottle 16 can be applied to any suitable mating devices and the ozonated water or fluid 46 can be used to disinfect fluid paths in and the surface areas around, devices or surfaces to be cleaned and disinfected or, as shown in FIG. 12 used as an irrigating fluid or treatment fluid in a dental procedure.

FIGS. 3 and 13 show one example of a charging system 10 with a bottle 38 of ozonated water 46 attached thereto. FIG. 3 shows the bottle cutaway so the ozone feed tube 18 and the ozonated water delivery tube 36 are readily visible. FIG. 4 is a view of FIG. 13 with the charging unit deleted so that a mounting bracket 48 for the upper portion 26 of the stopper can be seen. The bracket 48 is attached to the charging system 10 so that the bottle 16 with lower portion 24 can be readily separated from the upper portion 26.

FIGS. 6-10 show the various components of the stopper 22 in an assembled and exploded views. The dotted line 7-7 in FIG. 7 marks the location where the lower and upper portion 24, 26 separate.

Figure 7:
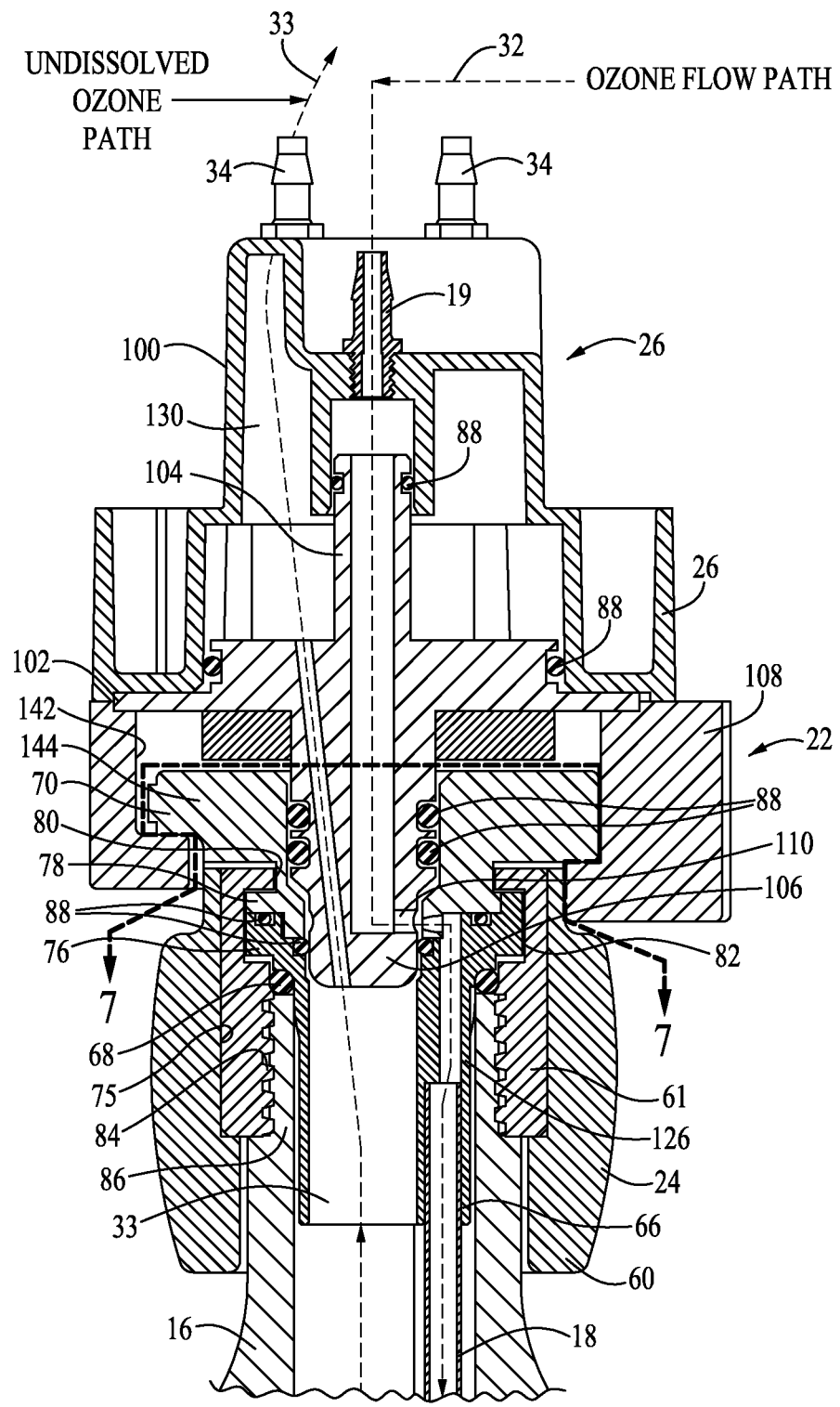
FIG. 7 is an enlarged cutaway view of the stopper showing the upper and lower stopper portions in their joined configurations including the ozone feed path shown as a dotted line.

Lower portion 24 comprises, going from the outside inwardly, an outer bottle nut 60, an inner bottle nut 61 which is split vertically into two half cylindrical section 62, 64 (or more than two partial cylindrical sections), a down spout 66 with a first O-ring 68 on the down spout 66 outer surface, and a lower cap 70. The outer surface of the two sections 62, 64 of the inner bottle nut 61 has vertical grooves 72 therein that mesh with vertical teeth 74 on the inner wall 75 of the outer bottle nut 60 so that, when assembled, rotation of the outer bottle nut 60 causes the inner bottle nut to also rotate. The down spout 66 has a circumferential flange 76 on its upper end. The lower cap has a matching flange 78 with a circumferential groove 80 above the flange 78. When assembled, a collar/groove arrangement 82 on the top end of the inner bottle nut 61 secures the down spot 66 to the bottom of the lower cap 70, as best shown in FIG. 7. The inner wall of the inner bottle nut has spiral grooves 84 to match spiral threads 86 on the top of the bottle 16 used to attach the stopper 22 to the bottle 16. Additional O-rings 88 are strategically placed throughout the assembly to seal potential points of ozone leakage. As best shown in FIG. 11, the ozone feed tube 18 and the delivery line 42 are attached to the bottom of the down spout with the inner lumen of each communicating with holes through the down spout 66.

Referring to FIGS. 6, 7, 8 and 10, the upper portion 26 comprises, proceeding from the top down, an upper cap 100, a distribution plate 102 with upper and lower tubular extensions 104, 106 and a locking collar 108. One or more fittings 34, through which undissolved ozone 33 leaves the bottle 16 and the stopper 22, are securely attached to openings in the top of the upper cap 100. The figures show two such fittings 34 but one fitting or more than two may be used. A similar appearing fitting which serves as the ozone feed tube connector 19 is also secured in a third opening in the top of the upper cap 100.

As best illustrated by the downward flow path of the ozone in FIG. 7, the upper portion of the downward ozone flow channel in the down spout 66 passes through the interior of the upper tubular extension 104 configured to receive the ozone flow, through the lower tubular extension 106 and out a side opening 110 into the top of the down spout 66. The interlocking components of the lower and upper portions 24, 26 also include various matching pins, holes, extensions, slots and grooves so that when the components are assembled they are placed in the proper orientation to other components to allow proper flow of the ozone through those various components.

Ozone fed into ozone feed tube connector 19 flows downward into the lumen in the upper tubular extensions 104. An O-ring 88 on the outer surface of the upper tubular extensions 104 prevents ozone from escaping from the intended flow path (see FIG. 7) In the embodiment shown, the upper tubular extensions 104 is integral with the distribution plate 102 and the lower tubular extensions 106 so that ozone flow that enters the upper tubular extension 104 continues downward through the lower extension 108 exiting through a side hole 110 (see ozone flow path in FIGS. 7 and 10). When properly assembled the side hole 110 is positioned directly adjacent to a hole (not shown) extending vertically from the inner wall to the outer wall of the lower portion of the lower cap 70 into a matching hole in the inner top edge of the down spout 66. The hole in the down spout leads to an inner channel 126 then extends vertically within the wall of the down spot and into the ozone delivery tube 18 secured to the bottom of the channel 126.

FIG. 11 is a bottom perspective view of the lower end of the stopper with the ozone feed tube 18 and the delivery line 42 extending downward. The bottom partially closed end of the lower tubular extensions 106 is shown in the center of the bottom view. The eyebrow shaped ozone exit 128 in the bottom of the lower tubular extensions 106 provides a means for the undissolved ozone 33 to pass through the lower tubular extensions 106, into a hollow space 130 within the upper cap and exit the fittings 34 for recycling or destruction. The flow path of the undissolved ozone 33 is also shown in FIG. 7.

Referring back to FIGS. 4-10 the locking collar 108 has one or more openings 140 and an internal groove 142 to receive a mating portion of the lower cap 70, namely wings 144 that extend radially outward therefrom. In one method of assembling the system for charging a bottle of water, the lower portion 24 is screwed onto the top of the bottle. The upper portion 26 is attached to the charger 10 and the ozone delivery tube 20 is attached to the feed tube connector 19. The lower cap is then placed in to the lower opening in the locking collar 108 with the wings 144 in the openings 140 and twisted so that the wings run along the internal groove 142 in the locking collar 108 resulting in the lower portion 24 being joined to the upper portion with proper alignment of the ozone flow paths for leak proof ozone transmission from the ozone generator to the diffuser 30 in the water in the bottle 16

Once adequate ozone is dissolved in the water 17, resulting in a usable ozonated water solution 46, the bottle 16 with the lower portion 24 of the stopper is separated from the upper section 26, as shown in FIG. 5, and a suitable ozonated water delivery system is attached to the bottle. FIG. 12 shows the bottle 16 with cap lower portion 24 positioned in a stand 120. Inserted into the top of the cap lower portion 24 is a power head 122 with a dental irrigator 124 attached thereto. The power head 122 provides means (not shown), such as a hand pump or a pressurized gas cartridge, to pressurize the air space above the ozonated water 46 in bottle 16 to force the ozonated water up the delivery tube 36 and then into the irrigator 124. Alternatively, the power head 122 may enclose a pump (not shown) to provide pressure or to draw the ozonated water 46 out of the bottle 16 and through the irrigator 126. One skilled in the art will recognize there are numerous techniques to move the ozonated water 46 from the bottle and numerous devices that can be attached to the bottle 16 or the power head for applying the ozonated water to objects or devices, for example for sterilization or cleaning purposes, or to provide the ozonated water for medical procedures.

Applications for the bottled ozonated water include the delivery through internal passages and lumens or onto external surfaces of medical treatment appliances and surfaces. Typical applications include, but are not limited to cleaning and disinfecting of dental units and dental water lines, the surfaces of medical and diagnostic devices and appliances, ENT treatment units, endoscopes, biopsy devices, veterinary treatment systems, heat exchangers, micro-filtration, ultra-filtration, and dialysis devices, reverse osmosis systems, food and food equipment, food processing appliances and machinery and food preparation surfaces. It is also known that ozonated water, when properly applied and adequate safety precautions are taken, has known benefits in medical procedures and particularly in dental procedures. One particular intended use of the devices and systems described herein is to provide bottled ozonated water for subsequent attachment to medical delivery devices such as irrigation systems used to delivery ozone into a patient's mouth during the performance of dental procedures to destroy bacteria, and other contaminants that can create medical problems following the completion of the procedure.

One skilled in the art, based on the description provided herein will recognize that various modifications may be made within the scope of the teachings herein to provide an assembly that functions in substantially the same manner. Further, one skilled in the art is well aware of the materials of construction reasonably necessary to assemble a device such as described herein for generating, transferring, temporarily storing and delivering ozone and ozonated water, particularly stainless steel, Teflon, plastics and silicon rubber and other ozone resistant or ozone stable materials.

I claim:

1. An improved system for delivering a liquid containing ozone dissolved therein, the ozone contained in the liquid being present in concentrations sufficient for decontaminating surfaces comprising;
- a generator assembly for producing gaseous ozone, the generator assembly comprising a generator for converting oxygen to ozone and providing an ozone containing gas stream, and an oxygen source for delivering an oxygen containing gas stream to the generator,
- a container for holding a liquid, the liquid suitable for receiving the ozone containing gas stream produced by the generator to form a liquid with ozone dissolved therein,
- a conduit having a first end attached to a gas exit port on the generator for delivering ozone containing gas stream from the generator to an interior of the container and into the liquid in the container so as to form a liquid containing dissolved ozone, and
- a container sealing device, comprising a closure assembly for attachment to an opening in the container to provide a pressure tight seal, the conduit passing through the closure assembly in a leak proof manner,
- wherein the improvement comprises said closure assembly comprising an upper portion and a lower portion, the lower portion separable from the upper portion while the lower portion remains secured in the container opening, the upper portion attached to the generator such that, when the upper portion and the lower portion are joined the ozone containing gas stream produced in the generator passes through aligned flowpaths in the joined upper and lower portion in a leak proof manner, the conduit having a second end located below an upper surface of the liquid in the container, the second end having a gas diffuser attached thereto for distributing the ozone containing gas stream into the liquid to create the liquid containing dissolved ozone therein, the lower portion when separated from the upper portion remaining attached to the container and delivering the liquid containing dissolved ozone therein without removal of the lower portion.

2. The system of claim 1 wherein the closure assembly further includes
   a. one or more openings, the one or more openings configured to allow removal from the container of undissolved ozone or delivery to the container of a pressurizing gas, and
   b. a dissolved ozone and water delivery tube extending from a bottom portion of the closure assembly to a point adjacent the bottom of the container, the point adjacent the bottom of the container being within the liquid in the container.

3. The system of claim 1 wherein the oxygen source for delivering an oxygen containing gas stream to the generator comprises a gas pump, bottled air or oxygen, or an oxygen generator.

4. The system of claim 1 further including a liquid level sensor to indicate the presence of liquid in the container.

5. The system of claim 1 wherein the ozone dissolved in the liquid forms a liquid with a dissolved ozone concentration of ≥2.0 ppm, said liquid deliverable to a surface to be decontaminated.

6. The system of claim 1 wherein the upper portion and lower portions of the closure assembly comprises a twist to lock connect/disconnect assembly to provide the flow path alignment.

7. The system of claim 6, wherein twist to lock connect/disconnect assembly provides an air tight seal on a top of the battle container.

* * * * *